United States Patent [19]
Esnouf

[11] Patent Number: 6,098,621
[45] Date of Patent: Aug. 8, 2000

[54] DISPOSABLE OXYGENATING DEVICE

[76] Inventor: Philip Stuart Esnouf, 4 Balfour St., Toorak, Victoria 3142, Australia

[21] Appl. No.: 09/043,234

[22] PCT Filed: Jul. 2, 1996

[86] PCT No.: PCT/AU96/00417

§ 371 Date: Sep. 25, 1998

§ 102(e) Date: Sep. 25, 1998

[87] PCT Pub. No.: WO97/10018

PCT Pub. Date: May 20, 1997

[30] Foreign Application Priority Data

Sep. 12, 1995 [AU] Australia ............... PN 5384

[51] Int. Cl.[7] .................................................. A61M 16/00
[52] U.S. Cl. ................... 128/205.13; 128/203.28; 128/205.14; 128/205.17
[58] Field of Search ............... 128/203.28, 204.26, 128/204.28, 205.13, 205.15, 205.17, 205.24, 205.14

[56] References Cited

U.S. PATENT DOCUMENTS

| | | |
|---|---|---|
| 2,208,633 | 7/1940 | Heidbrink . |
| 2,535,938 | 12/1950 | Lombard ............... 128/205.13 |
| 3,196,866 | 7/1965 | Adams . |
| 3,796,216 | 3/1974 | Schwarz ............... 128/205.13 |
| 3,960,148 | 6/1976 | Dryden ............... 128/205.13 |
| 4,029,093 | 6/1977 | Kohnke ............... 128/205.13 |
| 4,077,404 | 3/1978 | Elam ............... 128/205.13 |
| 4,374,521 | 2/1983 | Nelson et al. . |
| 4,774,941 | 10/1988 | Cook ............... 128/205.13 |
| 4,856,548 | 8/1989 | Paluch ............... 137/102 |
| 4,919,132 | 4/1990 | Miser ............... 128/205.17 |
| 5,163,424 | 11/1992 | Kohnke ............... 128/205.13 |
| 5,359,998 | 11/1994 | Lloyd ............... 128/203.11 |
| 5,485,835 | 1/1996 | Vande Streek et al. ............... 128/205.13 |
| 5,520,173 | 5/1996 | Kuhn ............... 128/205.13 |

FOREIGN PATENT DOCUMENTS

| | | |
|---|---|---|
| 33029/78 | 8/1979 | Australia . |
| 0 367 285A2 | 5/1990 | European Pat. Off. . |
| 2 326 943 | 5/1977 | France . |
| 2 614 207 | 10/1988 | France . |
| 2 696 350 | 4/1994 | France . |
| 1 784 600 | 8/1971 | Germany . |
| 24 24 798 | 11/1975 | Germany . |
| 550725 | 1/1943 | United Kingdom . |
| 2 139 099 | 11/1984 | United Kingdom . |
| WO 84/01295 | 4/1984 | WIPO . |

*Primary Examiner*—John G. Weiss
*Assistant Examiner*—Joseph F. Weiss
*Attorney, Agent, or Firm*—Seed Intellectual Property Law Group, PLLC

[57] ABSTRACT

A disposable oxygenating device comprising a body and a collapsible bag coupled thereto, the body including first coupling means being couplable to a source of oxygen, second coupling means being couplable to an endotracheal tube, laryngeal mask or the like, a connector to which the bag is connected, an oxygen duct in fluid communication with the first coupling means having an outlet orifice which in use delivers oxygen from the source of oxygen to inflate the bag with oxygen, and an outlet, the arrangement being such that, in use, during an inspiration cycle, oxygen from the gab passes through the second coupling means and, during an expiration cycle, expiration products pass through the body and are expelled through the outlet.

21 Claims, 3 Drawing Sheets

250 to 500 ml.
DISPOSABLE OXYGENATING DEVICE

TECHNICAL FIELD

This invention relates to a disposable oxygenating device.

BACKGROUND OF THE INVENTION

In the post operative treatment of patients, it is usually desirable to supply oxygen or oxygen enriched air to a patient for a period of say 5 to 15 minutes to assist in reoxygenating the patient to offset the effects of the anaesthetic. Usually oxygen is available in recovery rooms from suppliers which are capable of delivering oxygen at a rate of about 4 to 6 liters per minute. Unfortunately this is less than the rate of inspiration of a typical adult patient. Some attempts have been made to provide an oxygen storage device which can store oxygen from a relatively low capacity supply so as to be able to deliver the oxygen or oxygen enriched air to the patient at a relatively high rate during inspiration.

SUMMARY OF THE INVENTION

An object of the present invention is to provide a disposable oxygenating device which is capable of delivering oxygen or oxygen rich air to a patient at relatively high flow rates.

According to the present invention there is provided a disposable oxygenating device comprising a body and a collapsible bag coupled thereto, the body including at least first, second and third openings, the first opening being couplable to a source of oxygen, the second opening being couplable to an endotracheal tube or a laryngeal mask or the like, and the third opening being in fluid communication with the interior of the bag. The arrangement is such that in use oxygen enters the body through the first opening and fills the bag so that during the inspiration cycle of the patient, oxygen stored in the bag can be rapidly delivered through the second opening to the endotracheal tube or the laryngeal mask.

The invention also provides a disposable oxygenating device comprising a body and a collapsible bag coupled thereto, the body including first coupling means being couplable to a source of oxygen, second coupling means being couplable to an endotracheal tube, laryngeal mask or the like, a connector to which the bag is connected, an oxygen duct in fluid communication with the first coupling means having an outlet orifice which in use delivers oxygen from the source of oxygen to inflate the bag with oxygen, and an outlet, the arrangement being such that, in use, during an inspiration cycle, oxygen from the bag passes through the second coupling means and, during an expiration cycle, expiration products pass through the body and are expelled through said outlet.

The invention also provides a method of oxygenating a patient having an endotracheal tube or laryngeal mask applied to him or her using a disposable oxygenating device having an inflatable bag comprising coupling the device to the endotracheal tube or laryngeal mask continuously supplying oxygen to the bag thereby inflating the bag with oxygen, permitting the bag to collapse during an inspiration cycle of the patient whereby oxygen from the bag is delivered to the patient through the endotracheal tube or laryngeal mask, and providing an outlet in the device whereby during an expiration cycle products of expiration are permitted to escape the device.

It is preferred that the bag is formed from a film of plastics material. Preferably the material comprises high density polyethylene.

Preferably the film is about 15 microns in thickness.

The bag may have a vent hole near an end thereof remote from the body.

Preferably the bag has a capacity in the range 250 to 500 ml.

Preferably further, the body is injection moulded from plastics material and the bag is adhered, bonded or welded thereto.

It will be appreciated that the device can be constructed of low cost materials so that it is cheap enough for disposal after a single use. This thereby avoids the need for sterilisation and/or autoclaving.

BRIEF DESCRIPTION OF THE DRAWINGS

The invention will now be further described with reference to the accompanying drawings, in which.

DETAILED DESCRIPTION OF THE INVENTION

Figure 1:
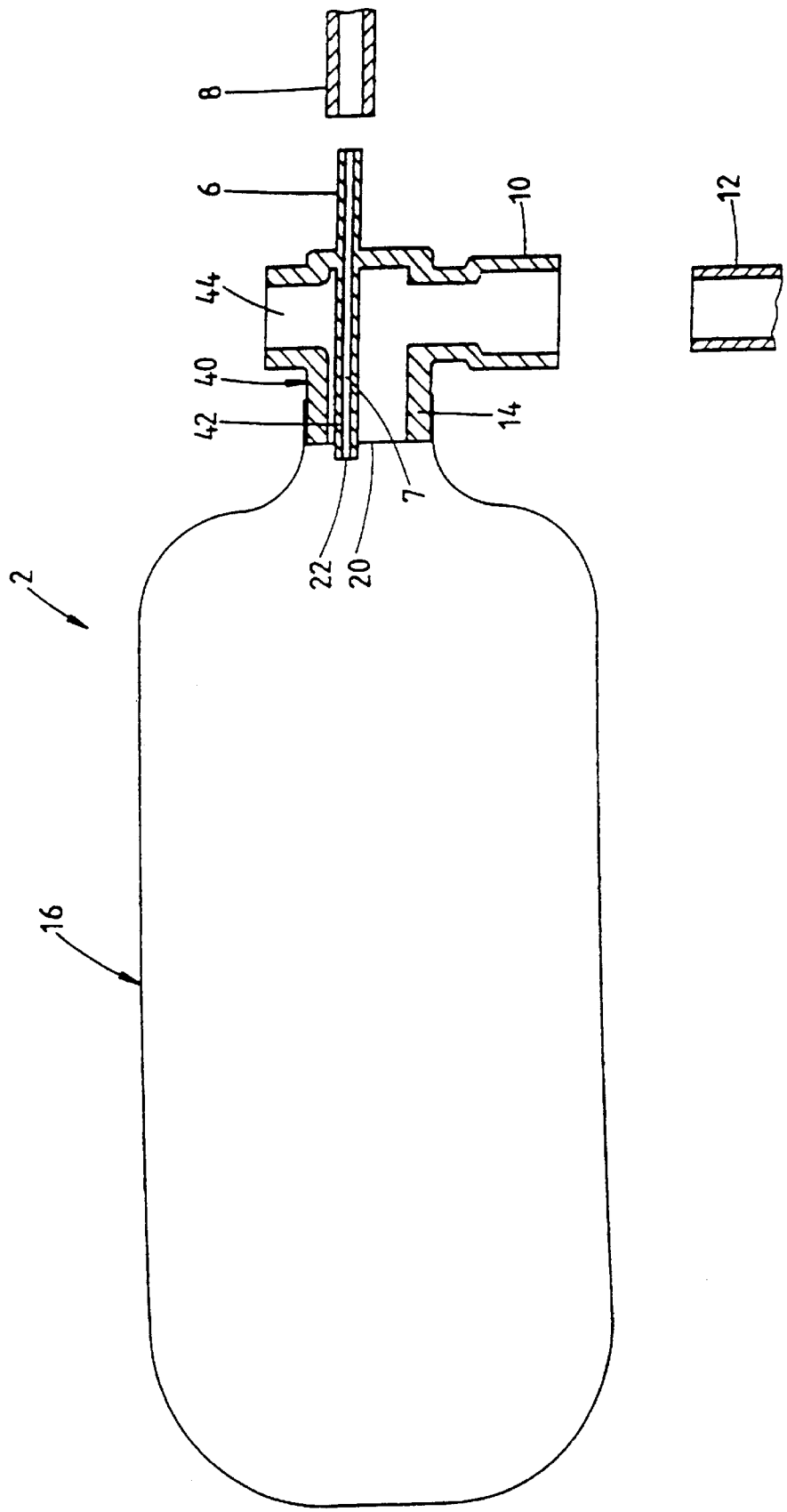
FIG. 1 is a schematic view of a first embodiment of a disposable oxygenating device constructed in accordance with the invention.

The disposable oxygenating device 2 shown in FIGS. 1 to 4 comprises an elbow 40 and a collapsible bag 16. The elbow 40 is preferably injection moulded from plastics material such as high density polyethylene. It generally comprises a hollow body having an inlet spigot 6 having an oxygen supply duct 7. The spigot 6 can be inserted in an oxygen supply tube 8 which is connected to a supply of compressed oxygen (not shown). The elbow 4 includes a tapered socket 10 which can be coupled to a male coupling 12 which is formed on the end of an endotracheal tube (oral or nasal) or laryngeal mask (not shown). The socket 10 has an internal bore which is compatible with complementary fittings on endotracheal tubes or laryngeal masks. Preferably the bore is 15 mm. The elbow 4 further includes a coupling connector or spigot 14 to which is connected a collapsible bag 16.

In the preferred form of the invention, the collapsible bag 16 is formed from high density polyethylene film having a thickness in the range from 5 to 15 microns and preferably 15 microns in thickness. The volume of the bag is in the range from 250 to 500 ml. Preferably the length is about 170 mm and the diameter about 80 mm. The bag 16 may be formed from a continuous tube of plastics material which is heat welded so as to have closed ends, one of which is heat welded or adhered to the spigot 14 and the other forms a closed end.

The disposable oxygenating device of the invention is particularly useful for oxygenating patients who are recovering from general anaesthesia which has been administered by a laryngeal mask or an endotracheal tube. The laryngeal mask or endotracheal tube are left in the patient and the socket 10 of the device is coupled to the coupling 12 of the mask or tube. An oxygen supply tube 8 which is coupled to a source of oxygen normally limited to a flow rate of about 4 to 6 liters a minute is connected to the inlet spigot 6. Oxygen passes through the inlet orifice 22 and may draw some air into the elbow 40 through the opening 44 so that the bag 16 is filled with oxygen enriched air. When the patient inspires, the oxygen rich air passes from the bag 16 through the socket 10 into the laryngeal mask or endotracheal tube. It will be noted that the internal passage from the coupling spigot 14 to the socket 10 is relatively wide and unconstricted so as to provide for good fluid flow therethrough. With the device of the invention, the rate of delivery of oxygen rich air can be optimum, say at about 20 liters per minute, which is normally much greater than that available in many recovery rooms.

In the preferred embodiment of the invention, the outlet orifice is located at the end of a conduit 42 which extends through the coupling spigot 14 so that oxygen passes directly into the interior of the bag 16. In this embodiment, the elbow 40 has a single relatively large opening 44 which is generally oppositely disposed to the socket 10, as seen in FIG. 2.

The elbow 40 may be injection moulded from suitable plastics material such as high density polyethylene. Moulding could be facilitated if the conduit 42 were not separately formed so as to extend through the coupling. In this case the oxygen passage 7 from the inlet spigot 6 could be moulded into the side wall of the elbow and it would still function correctly provided that the outlet orifice 22 opens into the interior of the bag 16 or is located close to the interior of the bag 16. The bag 16 may be heat seamed and trimmed into the shape of a bag. Its neck could be heat sealed onto the coupling spigot 14. The inlet spigot 6 could be formed with barbs or but may be smooth or provided with small serrations (not shown). The oxygen passage 7 through the opening 16 leading to the orifice 22 is preferably about 1.5 mm in diameter. The spigot 6 itself may have a 4 mm outer diameter. The socket 10 is preferably formed as a 15 mm tapered fitting for receipt of the end of an endotracheal tube, laryngeal mask or other device. The opening 44 preferably has a diameter of about 10 mm.

Figure 2:
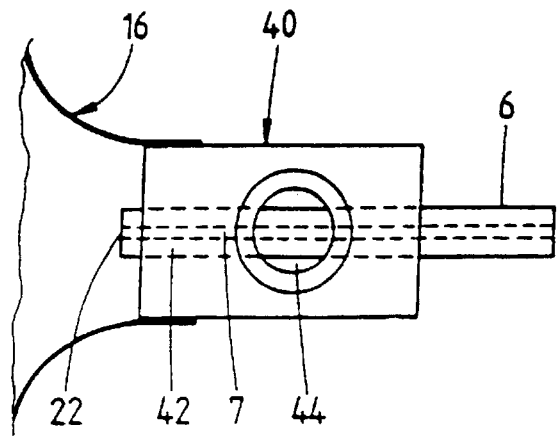
FIG. 2 is a plan view of the elbow shown in FIG. 1.
Figure 3:
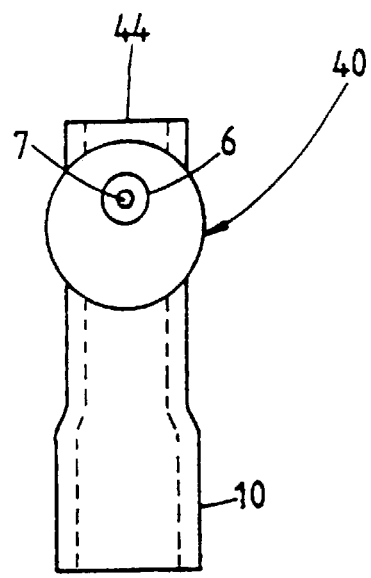
FIG. 3 is an end view of the elbow shown in FIG. 1.

In use of the device shown in FIGS. 1 to 3, the bag 16 is inflated with oxygen from the supply tube 8 through the orifice 22. The supply tube 8 delivers the oxygen at a nominal rate of say 6 liters per minute. During the inspiration cycle of the patient, oxygen collected in the bag 16 is delivered through the socket 10 to the tube 12. This preferably provides a volume of about 250 ml of oxygen or oxygen rich air to the patient.

The bag 16 refills with oxygen from the oxygen supply tube 8 during the pause between the end of inspiration and commencement of expiration. The expiratory air tends to pass directly from the socket 10 through the opening 44. This prevents significant dilution of the oxygen in the bag 16 by the expiratory fluid passing into the elbow 40 from the tube 12. Experiments have shown that the device shown in FIGS. 1 to 3 performs well because the rate of undiluted oxygen available from the bag 16 to the patient than is greater than that from the oxygen supply tube 8.

Figure 4:
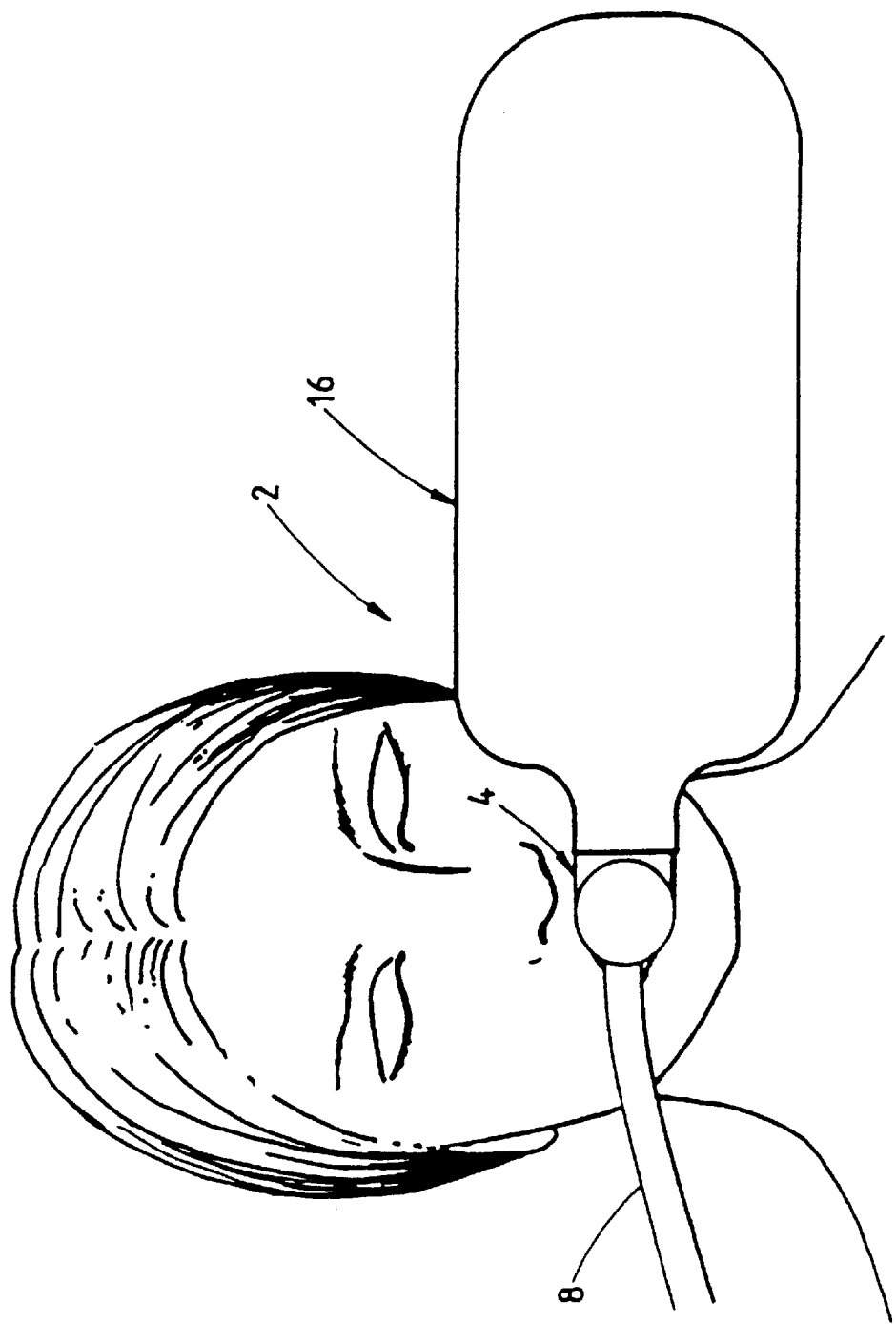
FIG. 4 schematically illustrates the manner in which the device is used.

FIG. 4 shows the preferred manner in which the device 2 is used. It will be seen that the bag 16 is located generally transversely to a reclining patient and the tube 8 extends on the opposite side of the patient. The endotracheal tube or laryngeal mask passes through the mouth of the patient in the usual way. In operation the bag 16 will collapse (or partly collapse) which provides a visual indication to recovery room staff that the patient is breathing.

It will be appreciated by those skilled in the art that the device of the invention can be made from inexpensive materials and is therefore cheap enough to be disposable. It does not need any valves which, if needed, could make manufacture more expensive and possibly compromise the reliability of the device.

As indicated above, the device can be used with oral or nasal endotracheal tubes or laryngeal masks. It is quite possible that the same device can be used in other applications such as for coupling to a tracheostomy tube.

Many modifications will be apparent to those skilled in the art without departing from the spirit and scope of the invention.

What is claimed is:

1. A disposable oxygenating device comprising a body and a collapsible bag coupled thereto, the body including first coupling means being couplable to a source of oxygen, second coupling means being couplable to an endotracheal tube or laryngeal mask, a connector to which the bag is connected, an oxygen duct in fluid communication with the first coupling means having an outlet orifice which in use delivers oxygen from the source of oxygen to inflate the bag with oxygen, and an outlet, the arrangement being such that, in use, during an inspiration cycle, oxygen from the bag passes through the second coupling means and, during an expiration cycle, expiration products pass through the body and are expelled through said outlet characterised in that the device does not include a valve.

2. A device as claimed in claim 1, wherein the outlet orifice is directed towards the interior of the bag.

3. A device as claimed in claim 1 or 2 wherein the outlet orifice is located adjacent to the bag.

4. A device as claimed in claim 3 wherein the oxygen duct is formed in a conduit which passes from the first coupling means through the body and terminates adjacent to the connector.

5. A device as claimed in claim 4 wherein the outlet is located generally opposite to the second coupling means.

6. A device as claimed in claim 1 wherein the body is moulded from plastics material.

7. A device as claimed in claim 6 characterised in that the body does not include any valves.

8. A device as claimed in claim 6 wherein the first coupling means comprises a spigot which can be inserted, in use, into an oxygen tube.

9. A device as claimed in claim 8 wherein the spigot has a nominal outer diameter of 4 mm.

10. A device as claimed in claim 9 wherein the second coupling means includes a 15 mm tapered socket.

11. A device as claimed in claim 10 wherein the outlet comprises a single opening 10 mm in diameter which is aligned with said tapered socket.

12. A device as claimed in claim 1 wherein the bag is formed from sheet plastics material.

13. A device as claimed in claim 12 wherein the sheet plastics material comprises high density polyethylene.

14. A device as claimed in claim 13 wherein the thickness of said sheet plastics material is in the range of approximately 5 to 15 microns, inclusive.

15. A device as claimed in claim 13 wherein the volume of the bag is about 250 ml when inflated.

16. A device as claimed in claim 15 wherein the bag is formed from an initially flat tube.

17. A disposable oxygenating device comprising a body and a collapsible bag, the collapsible bag having a surface and an opening therein, the body including first coupling means being couplable to a source of oxygen, second coupling means being couplable to an endotracheal tube or laryngeal mask, a connector to which the opening of the bag is connected, an oxygen duct in fluid communication with the first coupling means having an outlet orifice which in use delivers oxygen from the source of oxygen to inflate the bag with oxygen, and an outlet, the arrangement being such that, in use, during an inspiration cycle, oxygen from the bag passes through the second coupling means and, during an expiration cycle, expiration products pass through the body and are expelled through said outlet characterised in that the bag is formed from seamed plastics material and the surface of the bag is imperforate.

18. A device as claimed in claim 17 wherein the sheet plastics material is high density polypropylene.

19. A device as claimed in claim 18 wherein the thickness of said sheet plastics material is in the range of about 5 to 15 microns.

20. A device as claimed in claim 19 wherein the volume of the bag is about 250 ml when inflated.

21. A device as claimed in claim 20 wherein the bag is formed from an initially flat tube.

* * * * *